(12) United States Patent
Sema et al.

(10) Patent No.: US 10,610,308 B2
(45) Date of Patent: Apr. 7, 2020

(54) NAVIGATION GUIDEWIRE WITH INTERLOCKED COILS

(71) Applicant: Acclarent, Inc., Irvine, CA (US)

(72) Inventors: Ghislain G. Sema, Costa Mesa, CA (US); Mina W. Chow, Campbell, CA (US); Jetmir Palushi, Irvine, CA (US); Ketan P. Muni, San Jose, CA (US); Henry F. Salazar, Pico Rivera, CA (US)

(73) Assignee: Acclarent, Inc., Irvine, CA (US)

(*) Notice: Subject to any disclaimer, the term of this patent is extended or adjusted under 35 U.S.C. 154(b) by 0 days.

(21) Appl. No.: 15/861,959

(22) Filed: Jan. 4, 2018

(65) Prior Publication Data

US 2018/0214216 A1    Aug. 2, 2018

Related U.S. Application Data

(60) Provisional application No. 62/453,220, filed on Feb. 1, 2017.

(51) Int. Cl.
*A61B 5/00* (2006.01)
*A61B 34/20* (2016.01)
(Continued)

(52) U.S. Cl.
CPC .......... *A61B 34/20* (2016.02); *A61B 1/00158* (2013.01); *A61B 1/07* (2013.01);
(Continued)

(58) Field of Classification Search
CPC .... A61M 3/0295; A61M 29/02; A61M 25/09; A61M 2025/09083; A61M 2025/09191;
(Continued)

(56) References Cited

U.S. PATENT DOCUMENTS 4,538,622 A * 9/1985 Samson .......... A61M 25/09033
600/434
4,676,249 A * 6/1987 Arenas ............ A61M 25/09025
600/434
(Continued)

FOREIGN PATENT DOCUMENTS

EP        2 862 589 A1    4/2015
WO    WO 2016/171940 A1   10/2016

OTHER PUBLICATIONS

U.S. Appl. No. 62/453,220, entitled "Navigation Guidewire with Interlocked Coils," filed Feb. 1, 2017.
(Continued)

*Primary Examiner* — May A Abouelela
(74) *Attorney, Agent, or Firm* — Frost Brown Todd LLC

(57) ABSTRACT

An apparatus includes a proximal coil, a distal coil, a navigation sensor, and a wire. The proximal coil is formed by a wire wrapped in a helical configuration. The distal coil is formed by a wire wrapped in a helical configuration. At least one wrap at a proximal portion of the distal coil is interlocked with at least one wrap at a distal portion of the proximal coil, such that interlocking portions of the proximal and distal coils form a double helix configuration. The navigation sensor is located within the distal coil. The navigation sensor is configured to generate signals in response to movement within an electromagnetic field. The wire extends through the proximal coil. The wire is in electrical communication with the navigation sensor such that the wire is configured to communicate signals from the navigation sensor.

19 Claims, 13 Drawing Sheets

(51) Int. Cl.
*A61M 3/02* (2006.01)
*A61B 1/07* (2006.01)
*A61M 25/09* (2006.01)
*A61B 17/24* (2006.01)
*A61B 1/00* (2006.01)
*A61B 1/227* (2006.01)
*A61B 1/32* (2006.01)
*A61B 1/233* (2006.01)
*A61M 29/02* (2006.01)
*A61B 6/03* (2006.01)
*A61B 6/00* (2006.01)
*A61B 90/00* (2016.01)
*A61B 6/12* (2006.01)

(52) U.S. Cl.
CPC .............. *A61B 1/227* (2013.01); *A61B 1/233* (2013.01); *A61B 1/32* (2013.01); *A61B 17/24* (2013.01); *A61M 3/0295* (2013.01); *A61M 25/09* (2013.01); *A61B 6/032* (2013.01); *A61B 6/12* (2013.01); *A61B 6/488* (2013.01); *A61B 90/361* (2016.02); *A61B 2034/2051* (2016.02); *A61B 2034/2072* (2016.02); *A61M 29/02* (2013.01); *A61M 2025/09083* (2013.01); *A61M 2025/09191* (2013.01)

(58) Field of Classification Search
CPC ......... A61M 2025/09091; A61M 2025/09141; A61M 25/0045; A61B 34/20; A61B 1/07; A61B 6/032; A61B 2034/2051; A61B 17/1214; A61B 2017/1205; A61B 2017/00867; A61B 17/12109; A61B 2017/00477
USPC .................................... 600/300, 585
See application file for complete search history.

(56) References Cited

U.S. PATENT DOCUMENTS

| | | | | |
|---|---|---|---|---|
| 4,922,924 A * | 5/1990 | Gambale | ............... | A61M 25/09 600/434 |
| 4,934,380 A * | 6/1990 | de Toledo | ............ | A61M 25/09 600/434 |
| 5,174,295 A * | 12/1992 | Christian | ................. | A61B 8/06 600/468 |
| 5,271,415 A * | 12/1993 | Foerster | ............ | A61M 25/0905 600/434 |
| 5,282,478 A * | 2/1994 | Fleischhaker, Jr. | .......................... | A61M 25/0905 403/229 |
| 5,377,690 A * | 1/1995 | Berthiaume | .......... | A61M 25/09 600/585 |
| 5,421,348 A * | 6/1995 | Larnard | ............ | A61M 25/0905 600/434 |
| 5,520,194 A * | 5/1996 | Miyata | .................. | A61M 25/09 600/434 |
| 5,788,653 A * | 8/1998 | Lorenzo | ............ | A61M 25/0905 600/585 |
| 5,954,672 A * | 9/1999 | Schwager | ............ | A61B 5/6851 600/585 |
| 6,491,646 B1 * | 12/2002 | Blackledge | ........ | A61M 25/0905 600/585 |
| 6,527,732 B1 * | 3/2003 | Strauss | .................. | A61M 25/09 600/585 |
| 6,648,837 B2 * | 11/2003 | Kato | ..................... | A61M 25/09 600/585 |
| 7,077,811 B2 * | 7/2006 | Vrba | ..................... | A61M 25/09 600/585 |
| 7,186,223 B2 * | 3/2007 | Hiejima | ................. | A61M 25/09 600/585 |
| 7,637,875 B2 * | 12/2009 | Itou | ....................... | A61M 25/09 600/434 |
| 7,720,521 B2 | 5/2010 | Chang et al. | | |
| 8,123,722 B2 | 2/2012 | Chang et al. | | |
| 8,190,389 B2 | 5/2012 | Kim et al. | | |
| 8,239,003 B2 | 8/2012 | Akins | | |
| 8,320,711 B2 | 11/2012 | Altmann et al. | | |
| 8,425,537 B2 * | 4/2013 | Mitelberg | ........ | A61B 17/12022 606/139 |
| 8,702,626 B1 | 4/2014 | Kim et al. | | |
| 9,155,492 B2 | 10/2015 | Jenkins et al. | | |
| 9,167,961 B2 | 10/2015 | Makower et al. | | |
| 9,198,736 B2 | 12/2015 | Kim et al. | | |
| 9,968,762 B2 * | 5/2018 | Green | .................... | A61M 25/09 |
| 2007/0208252 A1 | 9/2007 | Makower | | |
| 2007/0219464 A1 * | 9/2007 | Davis | ................. | A61M 25/0138 600/585 |
| 2007/0219465 A1 * | 9/2007 | Cedro | ............... | A61M 25/0138 600/585 |
| 2008/0051676 A1 * | 2/2008 | Melsheimer | ....... | A61M 25/0905 600/585 |
| 2008/0183128 A1 | 7/2008 | Morriss et al. | | |
| 2010/0030031 A1 | 2/2010 | Goldfarb et al. | | |
| 2011/0004057 A1 | 1/2011 | Goldfarb et al. | | |
| 2011/0060214 A1 | 3/2011 | Makower | | |
| 2012/0071857 A1 | 3/2012 | Goldfarb et al. | | |
| 2012/0191070 A1 * | 7/2012 | Nishigishi | .............. | A61M 25/09 604/528 |
| 2012/0220896 A1 * | 8/2012 | Matsuo | .................. | A61M 25/09 600/585 |
| 2012/0253321 A1 * | 10/2012 | Tsunezumi | ............ | A61M 25/09 604/528 |
| 2012/0323145 A1 * | 12/2012 | Nagano | .................. | A61M 25/09 600/585 |
| 2014/0024968 A1 * | 1/2014 | Echarri | ................. | A61M 25/09 600/585 |
| 2014/0046302 A1 * | 2/2014 | Green | ................... | A61M 25/09 604/528 |
| 2014/0074141 A1 | 3/2014 | Johnson et al. | | |
| 2014/0200444 A1 | 7/2014 | Kim et al. | | |
| 2014/0364725 A1 | 12/2014 | Makower | | |
| 2016/0008083 A1 | 1/2016 | Kesten et al. | | |
| 2016/0310041 A1 * | 10/2016 | Jenkins | ................. | A61M 25/09 |
| 2016/0310042 A1 | 10/2016 | Kesten et al. | | |
| 2016/0310714 A1 | 10/2016 | Jenkins et al. | | |
| 2017/0120020 A1 | 5/2017 | Lin et al. | | |

OTHER PUBLICATIONS

International Search Report and Written Opinion dated May 9, 2018 for Application No. PCT/US2018/016077, 12 pgs.

* cited by examiner

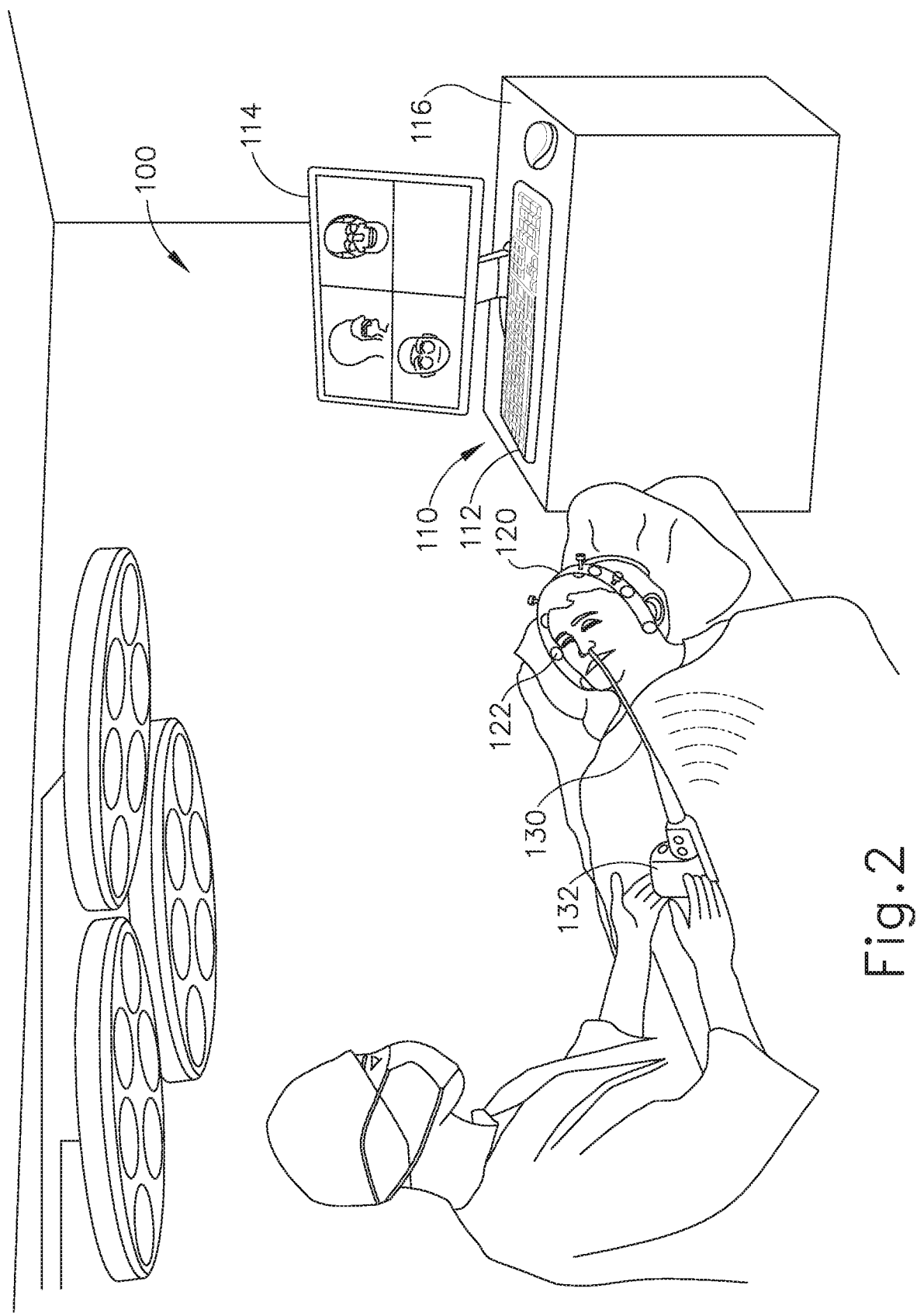

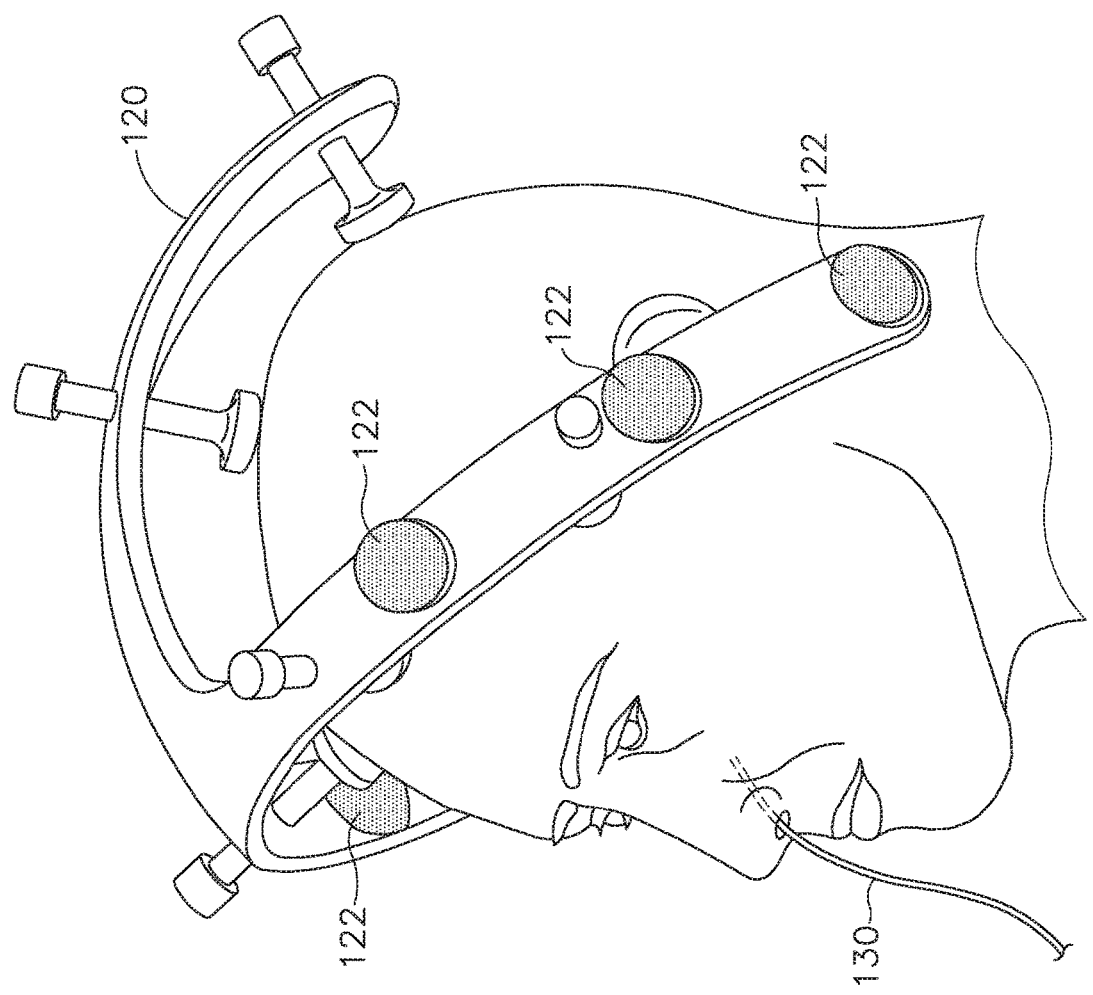

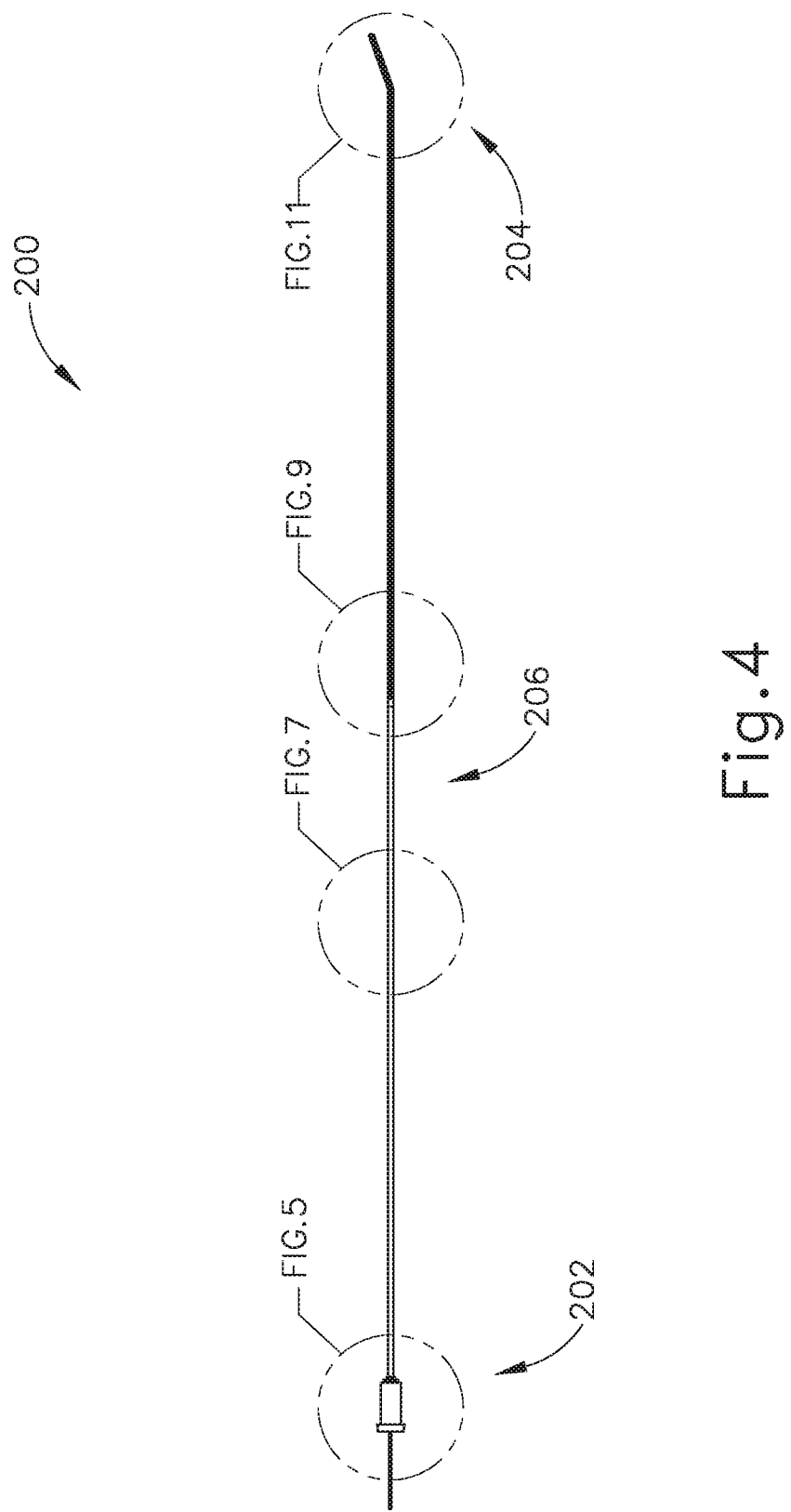

NAVIGATION GUIDEWIRE WITH INTERLOCKED COILS

PRIORITY

This application claims priority to U.S. Provisional Pat. App. No. 62/453,220, entitled "Navigation Guidewire with interlocked Coils," filed Feb. 1, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3-dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a schematic view of an exemplary sinus surgery navigation system;

FIG. 3 depicts a perspective view of the head of a patient, with components of the navigation system of FIG. 2;

FIG. 4 depicts a side elevational view of an exemplary navigation guidewire that may be incorporated into the dilation instrument assembly of FIG. 1A for use with the navigation system of FIG. 2;

Figure 1A:
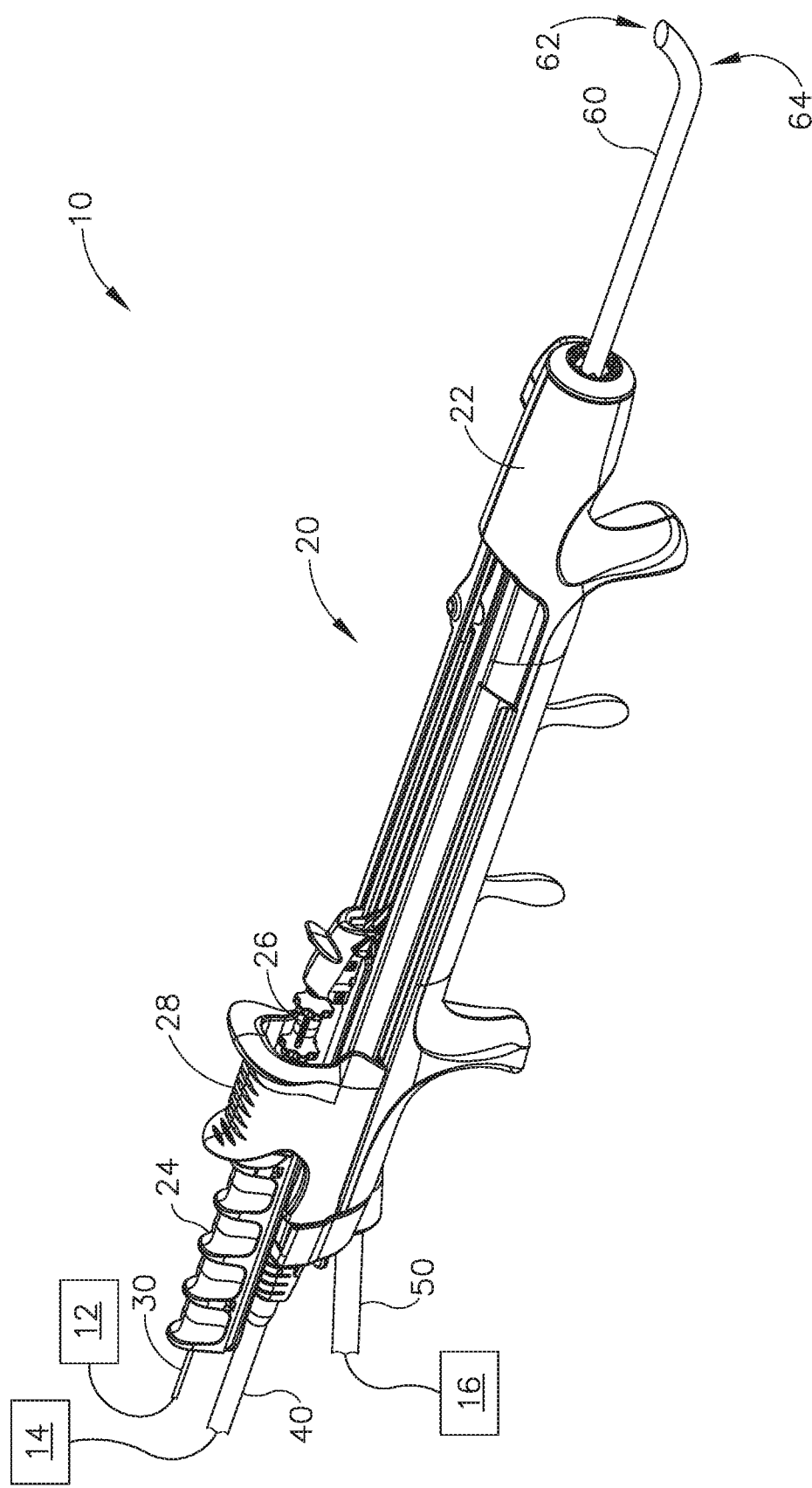
FIG. 1A depicts a perspective view of an exemplary dilation instrument assembly, with a guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows an exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) comprises a source of light. In some other versions, guidewire power source (12) is part of an IGS system as described below. In the present example, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22), Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
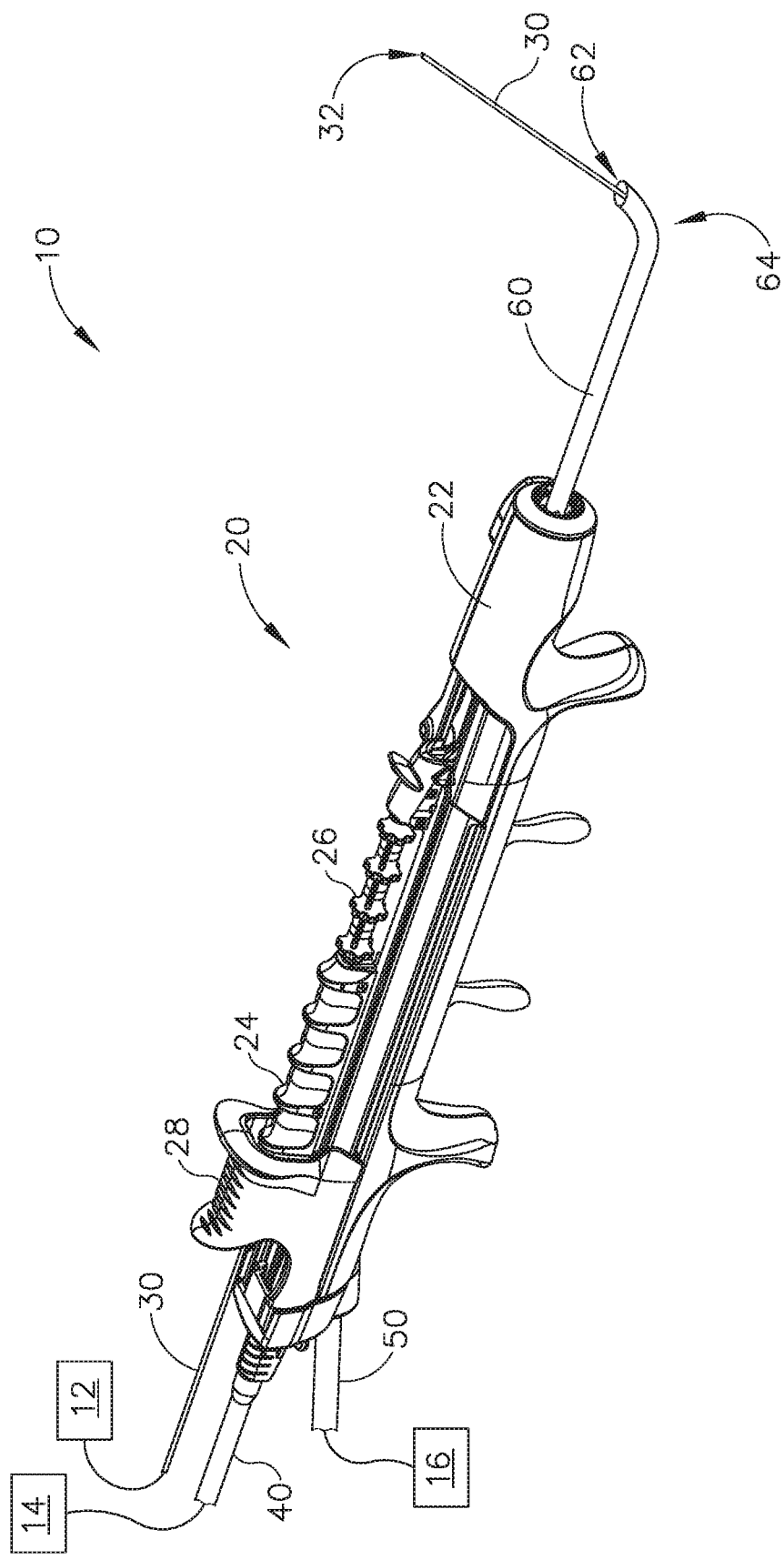
FIG. 1B depicts a perspective view of the dilation instrument assembly of FIG. 1A, with the guidewire in a distal position, and with the dilation catheter in the proximal position.

Dilation instrument (30) further comprises a guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to the distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32). This optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™ Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
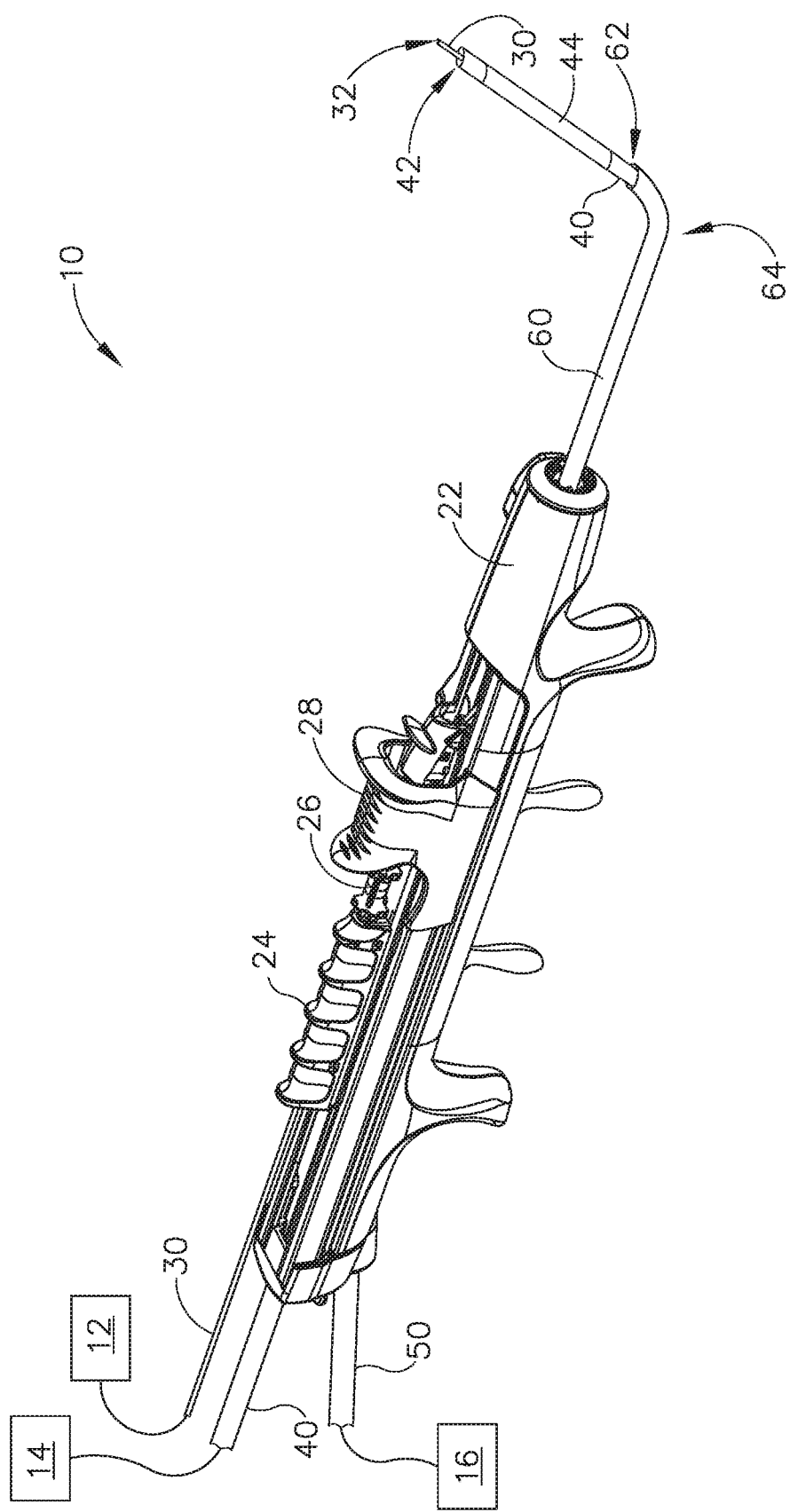
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
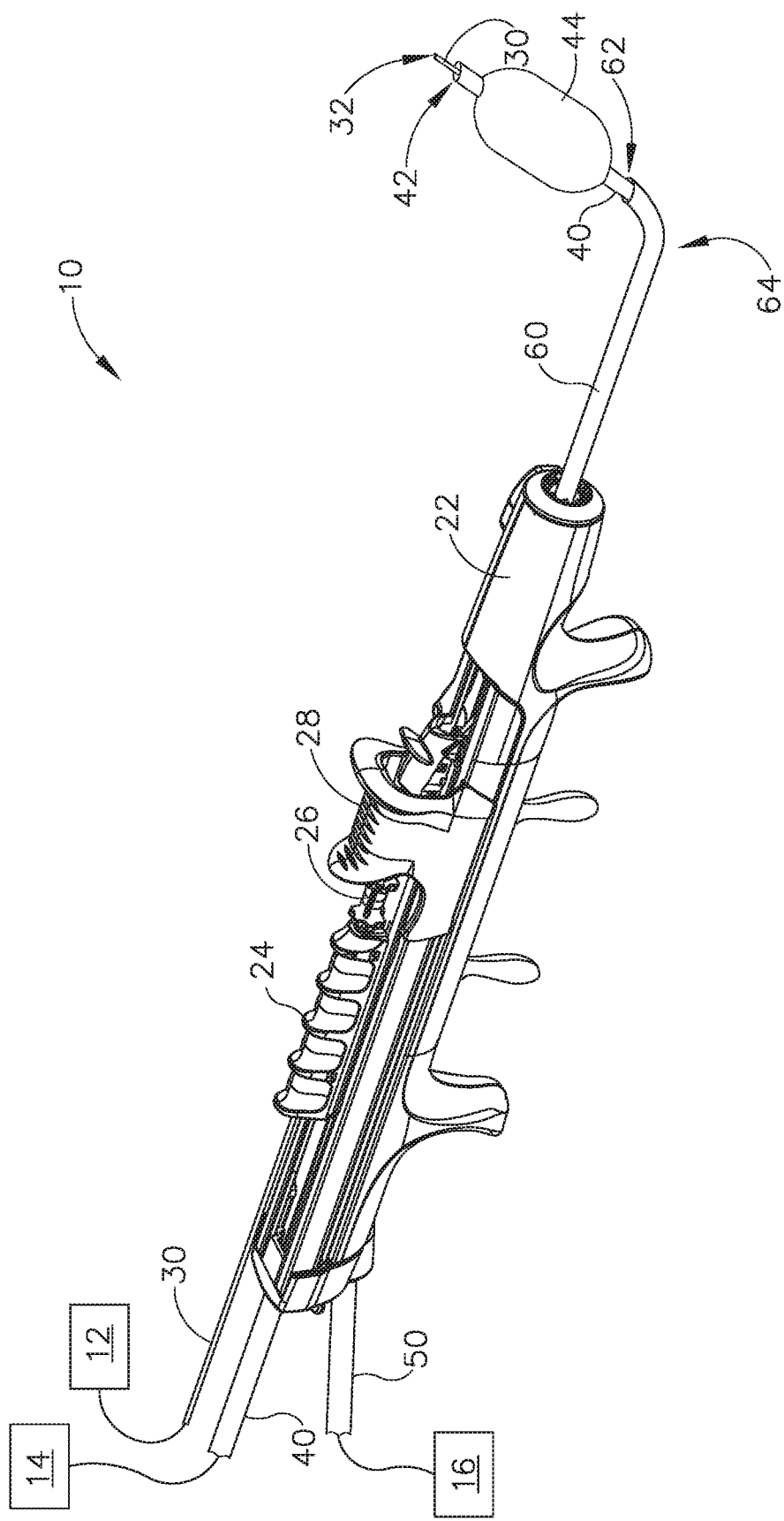
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured, and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar the Relieva Ultirra™ Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide member may be constructed and operable in accordance with at least some of the teachings of U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein; and/or U.S. Pub, No. 2012/0071857, entitled "Methods and Apparatus for Treating Disorders of the Sinuses," published Mar. 22, 2012, now abandoned, the disclosure of incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, now abandoned, the disclosure of which is incorporated by reference herein. Other suitable kinds of endoscopes that may be used with the various versions of dilation instrument assembly (10) described herein will be apparent to those of ordinary skill in the art.

II. Exemplary Image Guided Surgery Navigation System

FIG. 2 shows an exemplary IGS navigation system (100) whereby an ENT procedure may be performed using IGS. In some instances, IGS navigation system (100) is used during a procedure where dilation instrument assembly (10) that may be used to dilate the ostium of a paranasal sinus; or to dilate some other anatomical passageway (e.g., within the ear, nose, or throat, etc.). However, it should be understood that IGS navigation system (100) may be readily used in various other kinds of procedures.

In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (100) may be constructed and operable in accordance with at least some of the teachings of U.S. Pat. Pub. No. 2014/0364725, entitled "Systems and Methods for Performing image Guided Procedures within the Ear, Nose, Throat and Paranasal Sinuses," published Dec. 11. 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

IGS navigation system (100) of the present example comprises a set of magnetic field generators (122). Before a surgical procedure begins, field generators (122) are fixed to the head of the patient. As best seen in FIG. 3, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (30) described above, and may include a sensor (not shown) that is responsive to movement within the fields generated by field generators (122). In particular, signals generated by the sensor of navigation guidewire (130) may be processed by processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of IGS navigation system (100). It should be understood that, when used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130), including but not limited to the exemplary alternative dilation catheter (200) described below.

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 2 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (00) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

III. Exemplary Alternative Guidewire

FIG. 4 shows an exemplary alternative guidewire (200) that may be incorporated into dilation instrument assembly (10), in place of guidewire (30). Except as otherwise described below, guidewire (200) may be configured and operable just like guidewire (30). Guidewire (200) is configured to provide IGS navigation system (100) compatibility to dilation instrument assembly (10). It should therefore be understood that guidewire (200) may also be configured and operable just like navigational guidewire (130), except as otherwise described below.

Figure 5:
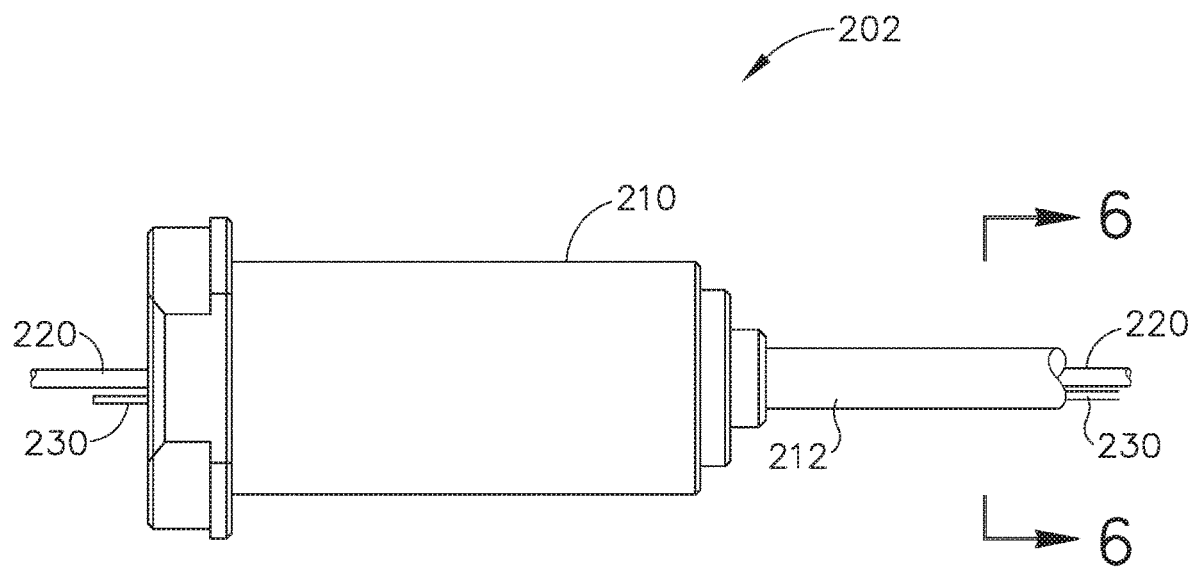
FIG. 5 depicts an enlarged side elevational view of the proximal region of the guidewire of FIG. 4 indicated by the "FIG. 5" broken line circle of FIG. 4.
Figure 6:
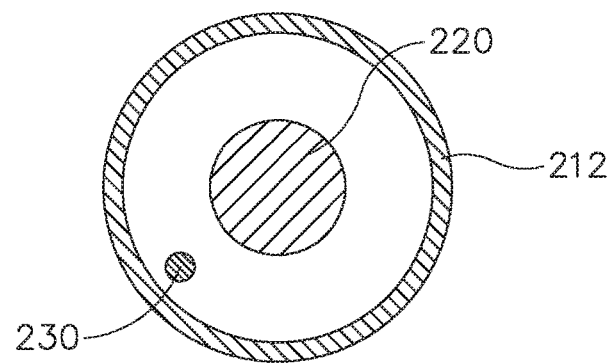
FIG. 6 depicts a cross-sectional end view of the guidewire of FIG. 4, taken along line 6-6 of FIG. 5.

Guidewire (200) of the present example has a proximal end (202), a distal end (204), and an intermediate region (206) extending between ends (202, 204). As best seen in FIGS. 5-6, a proximal portion of guidewire (200) includes a coupling member (210) and a tubular member (212). Coupling member (210) is configured to couple with a portion of IGS navigation system (100). For instance, coupling member (210) may be configured to couple with a console assembly containing processor (110). In some other versions, coupling member (210) is configured to couple with guidewire slider (24) and guidewire spinner (26). Other structures with which coupling member (210) may be coupled will be apparent to those of ordinary skill in the art in view of the teachings herein. In addition, while coupling member (210) of the present example has a cylindraceous body with an annular flange, other suitable configurations that may be used. for coupling member (210) will be apparent to those of ordinary skill in the art in view of the teachings herein.

Tubular member (212) extends distally from coupling member (210). By way of example only, tubular member (212) may be formed of a semi-flexible stainless steel cable tube that is configured to provide push-ability to guidewire (200). By way of further example only, tubular member (212) may have an outer diameter of approximately 0.0345 inches and an inner diameter of approximately 0.0225 inches. Alternatively, any other suitable dimensions may be used. In some variations, tubular member (212) is made of a flexible polymeric material. Various suitable materials that may be used to form tubular member (212) will be apparent to those of ordinary skill in the art in view of the teachings herein. As best seen in FIG. 6, a sensor wire (220) and a ground wire (230) are positioned within tubular member (212). Sensor wire (220) is configured to communicate signals from a sensor coil (222), which will be described in greater detail below, to IGS navigation system (100). It should therefore be understood that sensor wire (220) is in communication with sensor coil (222) and IGS navigation system (100). In the present example, sensor wire (220) has an outer diameter of approximately 0.022 inches. Ground wire (230) is configured to provide electrical grounding for electrically conductive components of guidewire (200), which may in turn substantially prevent interference in the signal communicated along sensor wire (220). The proximal end of ground wire (230) may be coupled with IGS navigation system (100) or any other suitable source of electrical ground. The distal end of ground wire (230) is coupled with a solder joint (214), which will be described in greater detail below.

Figure 7:
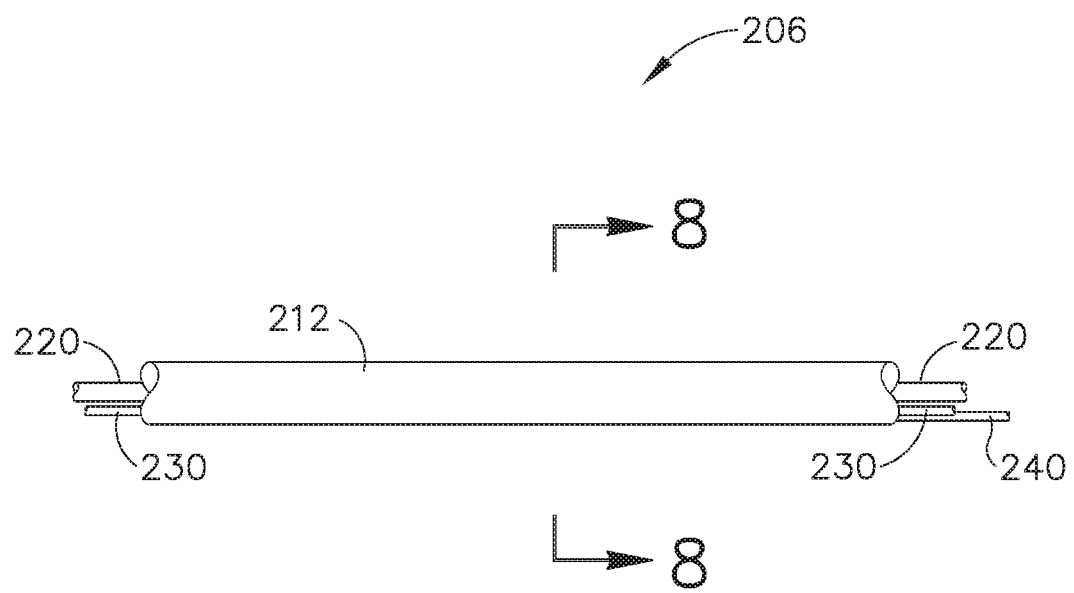
FIG. 7 depicts an enlarged side elevational view of the first intermediate region of the guidewire of FIG. 4 indicated by the "FIG. 7" broken line circle of FIG. 4.
Figure 8:
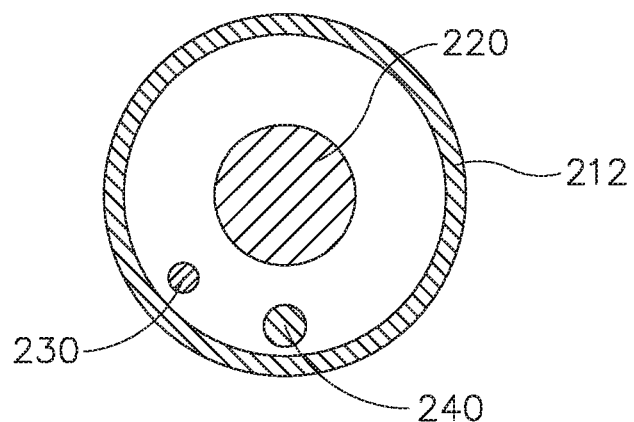
FIG. 8 depicts a cross-sectional end view of the guidewire of FIG. 4, taken along line 8-8 of FIG. 7.

FIGS. 7-8 show a first portion of intermediate region (206) of guidewire (200). Tubular member (212) extends along the full length of this portion. Sensor wire (220) and ground wire (230) also extend along the full length of this portion. A core wire (240) is secured to tubular member (212) in this portion. In particular, a proximal end of core wire (240) is secured to the inner wall of tubular member (212). Core wire (240) is formed of a non-extensible material (e.g., nitinol) that provides strength to the region of guidewire (200) along which core wire (240) extends. In particular, core wire (240) prevents guidewire (200) from stretching longitudinally along the length through which core wire (240) extends. While core wire (240) is non-extensible in this example, core wire (240) is flexible. Moreover, other than the proximal and distal ends of core wire (240), the intermediate region of core wire (240) is not fixedly secured within guidewire (200). Thus, core wire (240) does not adversely affect the lateral flexibility of guidewire (200). By way of example only, the proximal end of core wire (240) may be secured to the inner wall of tubular member (212) via an adhesive, via an epoxy, or using any other suitable means or techniques as will be apparent to those of ordinary skill in the art view of the teachings herein.

Figure 9:
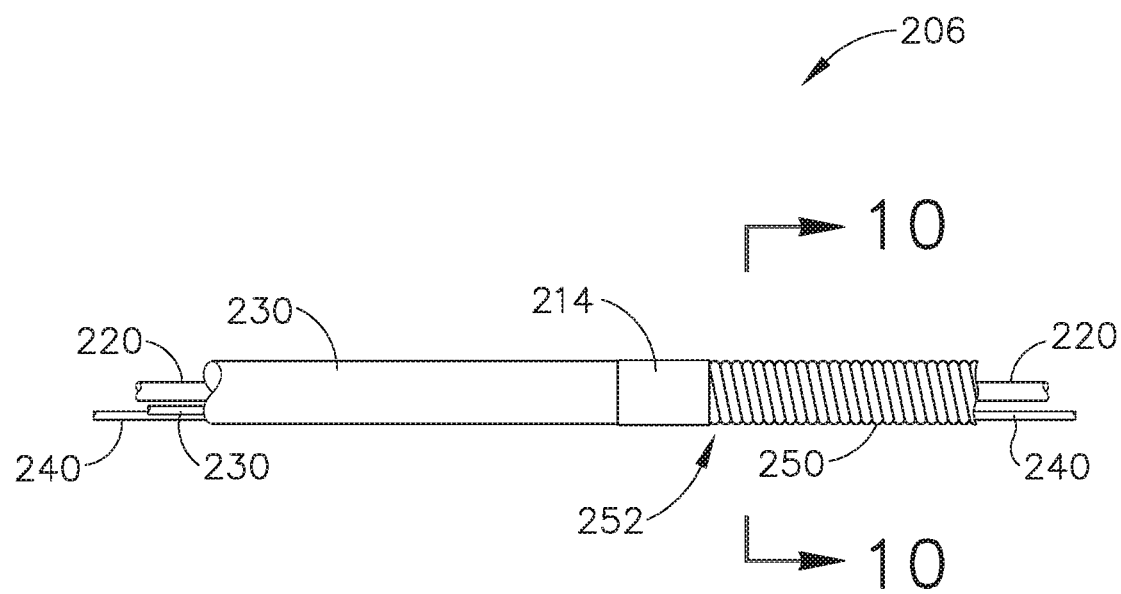
FIG. 9 depicts an enlarged side elevational view of the second intermediate region of the guidewire of FIG. 4 indicated by the "FIG. 9" broken line circle of FIG. 4.
Figure 10:
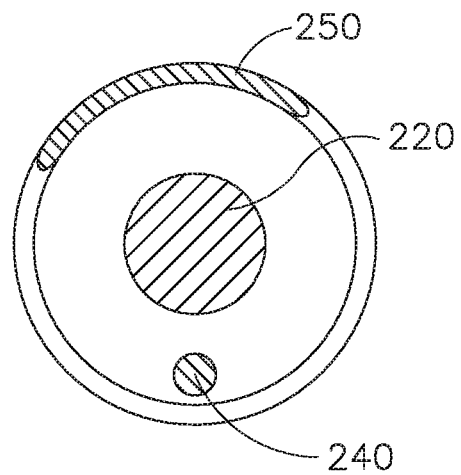
FIG. 10 depicts a cross-sectional end view of the guidewire of FIG. 4, taken along line 10-10 of FIG. 9.

FIGS. 9-10 show a second portion of intermediate region (206) of guidewire (200). In this portion, tubular member (212) terminates in solder joint (214). A proximal end (252) of a proximal coil (250) also terminates in solder joint (214). Solder joint (214) thus joins tubular member (212) with proximal coil (250). By way of example only, solder joint (21.4) may be formed of tin-silver solder. Alternatively, any other suitable material(s) may be used.

in the present example, proximal coil (250) is formed of a metallic wire (e.g., stainless steel) wrapped in a helical configuration. However, it should be understood that any suitable material(s) and configuration(s) may be used to form proximal coil (250). The distal end of ground wire (230) also terminates in solder joint (214). Solder joint (214) thus provides an electrical ground path from proximal coil (250) to ground wire (230). As best seen in FIG. 10, sensor wire (220) and core wire (240) pass through solder joint (214), continuing distally past the region portion of guidewire (200) shown in FIG. 9.

Figure 11:
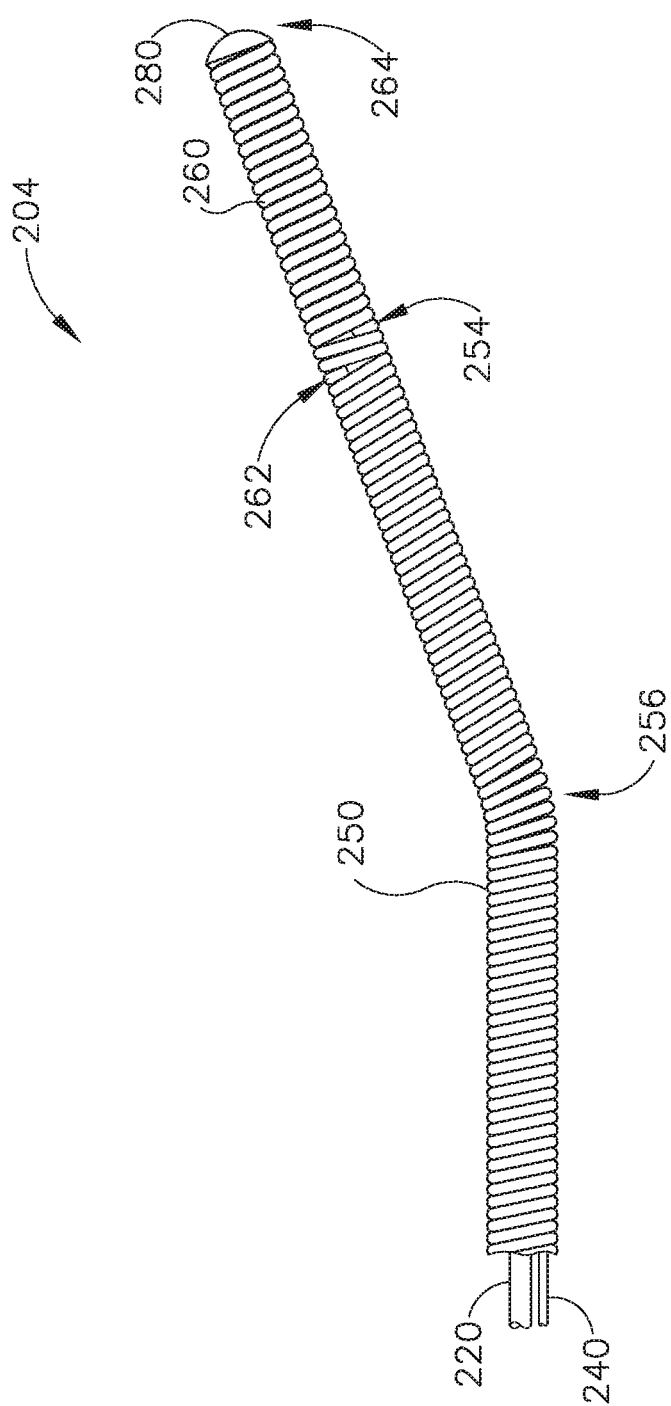
FIG. 11 depicts an enlarged side elevational view of the distal region of the guidewire of FIG. 4 indicated by the "FIG. 11" broken line circle of FIG. 4.
Figure 12:
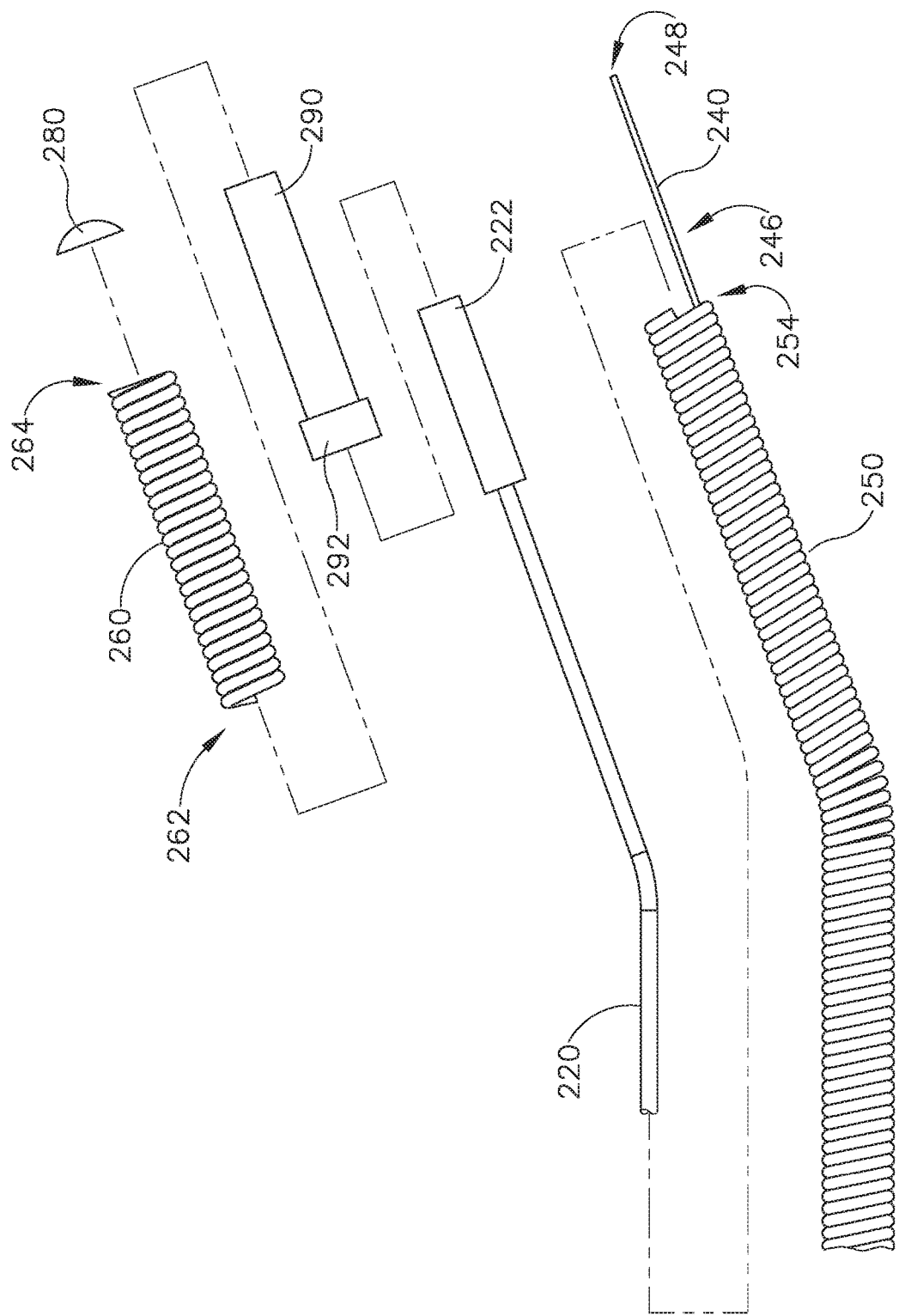
FIG. 12 depicts an exploded side elevational view of the distal portion of FIG. 11.

FIGS. 11-12 show distal end (204) of guidewire (200). Distal end (204) includes a distal coil (260). In the present example, distal coil (260) is formed of a metallic wire (e.g., stainless steel) wrapped in a helical configuration. However, it should be understood that any suitable material(s) and configuration(s) may be used to form distal coil (260). In the present example, the proximal end (262) of distal coil (260) is joined with the distal end (254) of proximal coil (250). In particular, ends (254, 262) are joined together in an interlocking fashion, such that the overlapping regions of coils (250, 260) form a double helix. By way of example only, the interlocking regions of ends (254, 262) may extend along approximately one to two full coil wraps of coils (250, 260). By way of further example only, the interlocking regions of ends (254, 262) may extend along a length between approximately 0.5 mm and approximately 0.75 mm.

In the present example, coils (254, 262) have the same outer diameter but different inner diameters. By way of example only, coils (250, 260) may both have an outer diameter of approximately 0.0345 inches, with proximal coil (250) having an inner diameter of approximately 0.0225 inches, and with distal coil (260) having an inner diameter of approximately 0.0265 inches. Alternatively, any other suitable diameters may be used. Also in the present example, proximal coil (250) has a length of approximately 4.5 inches; while distal coil (260) has a length of approximately 4.25 mm. Alternatively, coils (250, 260) may have any other suitable lengths. Also in the present example, proximal coil (250) has an open pitch of approximately 0.75 mm, in which the open pitch of distal coil (260) is interlocked with a corresponding open pitch, though any other suitable pitch may be used.

Also in the present example, a ring of solder (292) is applied to the interlocking regions of coils (250, 260) to further secure the interlocking regions of coils (250, 260) together. By way of example only, ring of solder (292) may be formed of tin-silver solder. Alternatively, any other suitable material(s) may be used.

Figure 13:
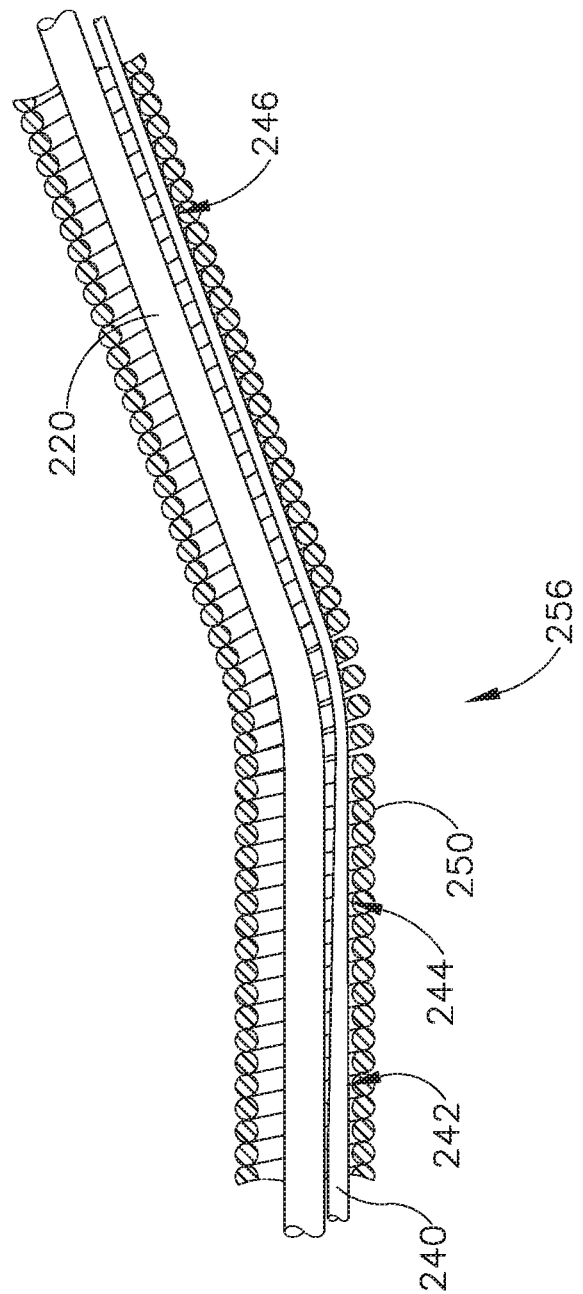
FIG. 13 depicts a cross-sectional side view of a bent region of the distal portion of FIG. 11.

As also shown in FIGS. 11-13, proximal coil (250) includes a preformed bend (256) formed between ends (252, 254). Bend (256) may be bent at an angle in accordance with bend angles known in the art of guidewires that are used in ENT surgical procedures. As best seen in FIG. 13, core wire (240) extends along the length of bend (256). As also seen in FIG. 13, core wire (240) tapers just proximal to bend (256). In particular, core wire (240) has a proximal region (242) that has an outer diameter that is larger than the outer diameter of a distal region (246), with a tapered region (244) providing a smooth transition between these outer diameters along bend (256). By way of example only, proximal region (242) may have an outer diameter of approximately 0.0095 inches or approximately 0.10 inches. By way of further example only, distal region (246) may be flattened to a thickness of approximately 0.0027 inches. Various suitable diameters, thicknesses, and taper angles that may be used along tapered region (244) will be apparent to those of ordinary skill in the art in view of the teachings herein.

It should be understood that the reduction of diameter (or flattening) of distal region (246) along bend (256) may facilitate achievement of the bend angle of bend (256) by core wire (240). It should also be understood that the reduced outer diameter (or flattening) of distal region (246), in conjunction with the enlarged inner diameter of distal coil (260), provides sufficient clearance to enable distal end (248) of core wire (240) to be secured by ring of solder (292) in distal coil (260); and to accommodate sensor (222) as described below.

As best seen in FIG. 12, a sensor (222) is located at the distal end of sensor wire (220). In the present example, sensor (222) comprises a single axis coil that is configured to generate signals as sensor (222) moves within an electromagnetic field. Sensor (222) is thus configured to cooperate with IGS navigation system (100) to provide position data relating to distal end (204) of guidewire (200). Various suitable components and configurations that may be incorporated into sensor (222) will be apparent to those of ordinary skill in the art in view fo the teachings herein. In the present example, sensor (222) is positioned such that sensor (222) is located in distal coil (260). In particular, an adhesive (290) is used to secure the outer diameter of sensor (222) to the inner diameter of distal coil (260). In the example shown the proximal end of adhesive (290) is positioned adjacent to the distal end of ring of solder (292). However, it should be understood that any other suitable spatial relationship may be used.

As also shown in FIG. 12, a tip member (280) is secured to the distal end (264) of distal coil (260). Tip member (280) has an atraumatic, dome shape in the present example. In some versions, tip member (280) is formed by adhesive (290). In some other versions, tip member (280) is formed as a separate piece (e.g., of a polymer) and is then secured to distal end (264), secured to adhesive (290), or secured to sensor (222). Other suitable ways in which tip member (280) may be formed and secured will be apparent to those of ordinary skill in the art in view of the teachings herein.

In some versions, at least a portion of the length of guidewire (200) (e.g., approximately 7 inches) is coated in one or more materials. By way of example only, at least a portion of the length of guidewire (200) may be coated in silicone. Other suitable materials that may be used as a coating for guidewire (200) will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a proximal coil, wherein the proximal coil is formed by a wire wrapped in a helical configuration; (b) a distal coil, wherein the distal coil is formed by a wire wrapped in a helical configuration, wherein at least one wrap at a proximal portion of the distal coil is interlocked with at least one wrap at a distal portion of the proximal coil, such that interlocking portions of the proximal and distal coils form a double helix configuration; (c) a navigation sensor located within the distal coil, wherein the navigation sensor is configured to generate signals in response to movement within an electromagnetic field; and (d) a wire extending through the proximal coil, wherein the wire is in electrical communication with the navigation sensor such that the wire is configured to communicate signals from the navigation sensor.

EXAMPLE 2

The apparatus of Example 1, further comprising a tubular member joined to a proximal end of the proximal coil, wherein the wire further extends through the tubular member.

EXAMPLE 3

The apparatus of Example 2, wherein the tubular member is formed of a metal material.

EXAMPLE 4

The apparatus of any one or more of Examples 2 through 3, further comprising a core wire, wherein the core wire is formed of a non-extensible material, wherein a proximal end of the core wire is secured to the tubular member.

EXAMPLE 5

The apparatus of Example 4, wherein a distal end of the core wire is secured to the distal coil.

EXAMPLE 6

The apparatus of any one or more of Examples 1 through 5, further comprising a ground wire, wherein the ground wire is secured to the proximal coil, wherein the ground wire is configured to provide electrical ground to the proximal coil.

EXAMPLE 7

The apparatus of any one or more of Examples 1 through 6, wherein the proximal coil includes a preformed bend, wherein the preformed bend is located proximal to a distal end of the proximal coil.

EXAMPLE 8

The apparatus of Example 7, further comprising a core wire, wherein the core wire is formed of a non-extensible material, wherein the core wire extends through the preformed bend of the proximal coil.

EXAMPLE 9

The apparatus of Example 8, wherein the core wire has a first region with a first outer diameter, a second region with a second outer diameter, and a taper extending from the first region to the second region.

EXAMPLE 10

The apparatus of Example 9, wherein the first outer diameter is proximal to the preformed bend.

EXAMPLE 11

The apparatus of Example 10, wherein the taper is proximal to the preformed bend.

EXAMPLE 12

The apparatus of any one or more of Examples 1 through 11, wherein the proximal coil defines an outer diameter, wherein the distal coil defines an outer diameter, wherein the outer diameter of the proximal coil is equal to the outer diameter of the distal coil.

EXAMPLE 13

The apparatus of Example 12, wherein the outer diameter of the proximal coil is approximately 0.0345 inches, wherein the outer diameter of the distal coil is approximately 0.0345 inches

EXAMPLE 14

The apparatus of any one or more of Examples 1 through 13, wherein the proximal coil defines an inner diameter, wherein the distal coil defines an inner diameter, wherein the inner diameter of the distal coil is larger than the inner diameter of the proximal coil.

EXAMPLE 15

The apparatus of Example 14, wherein the inner diameter of the proximal coil is approximately 0.0225 inches, wherein the inner diameter of the distal coil is approximately 0.0265 inches.

EXAMPLE 16

The apparatus of any one or more of Examples 1 through 15, wherein the navigations sensor comprises a single axis coil.

EXAMPLE 17

The apparatus of any one or more of Examples 1 through 16, further comprising: (a) a guide member, wherein the proximal and distal coils are configured to translate relative to the guide member; and (b) a dilation catheter slidably disposed about the proximal coil, wherein the dilation catheter includes an expandable dilator.

EXAMPLE 18

An apparatus, comprising: (a) a body; (b) a guide extending distally from the body; (c) a guidewire slidably disposed relative to the guide, wherein the guidewire comprises: (i) a proximal coil, wherein the proximal coil is formed by a wire wrapped in a helical configuration, (ii) a distal coil, wherein the distal coil is formed by a wire wrapped in a helical configuration, wherein at least one wrap at a proximal portion of the distal coil is interlocked with at least one wrap at a distal portion of the proximal coil, such that interlocking portions of the proximal and distal coils form a double helix configuration, and (iii) a navigation sensor located within the distal coil, wherein the navigation sensor is configured to generate signals in response to movement within an electromagnetic field; and (d) a dilation catheter slidably disposed relative to the guidewire, wherein the dilation catheter includes an expandable dilator.

EXAMPLE 19

The apparatus of Example 18, further comprising an image guidance system in communication with the navigation sensor, wherein the image guidance system is configured to render an image with a representation of a position of the navigation sensor in relation to a patient.

EXAMPLE 20

An apparatus comprising: (a) a proximal coil, wherein the proximal coil is formed by a wire wrapped in a helical configuration, wherein the proximal coil has a bent region located proximal to a distal end of the proximal coil; (b) a distal coil, wherein the distal coil is formed by a wire wrapped in a helical configuration, wherein at least one wrap at a proximal portion of the distal coil is interlocked with at least one wrap at a distal portion of the proximal coil, such that interlocking portions of the proximal and distal coils form a double helix configuration; and (c) a core wire extending through the proximal coil, wherein the core wire has a first region with a first outer diameter, a second region with a second outer diameter, and a taper extending from the first region to the second region, wherein the first outer diameter is proximal to the preformed bend.

EXAMPLE 21

A method of using the apparatus of any one or more of Examples 1 through 17, the method comprising: (a) inserting a distal portion of the apparatus into a head of a patient, wherein the distal portion includes the distal coil and the navigation sensor; (b) activating an electromagnetic field around the head of the patient; (c) tracking movement of the navigation sensor based on signals generated in response to movement of the navigation sensor within the electromagnetic field.

EXAMPLE 22

The method of Example 21, further comprising: (a) advancing a dilator along the distal portion of the apparatus to position the dilator in an anatomical passageway within the head of the patient; and (b) expanding the dilator to thereby dilate the anatomical passageway.

EXAMPLE 23

The method of Example 22, wherein the anatomical passageway is selected from the group consisting of a sinus ostium, a frontal recess, or a Eustachian tube.

EXAMPLE 24

A method of using the apparatus of any one or more of Examples 18 through 19, the method comprising: (a) generating an electromagnetic field around a head of a patient; (b) inserting a distal portion of the guide into the head of the patient; (c) advancing the guidewire distally relative to the guide to thereby position the distal coil and the navigation sensor in the head of the patient; and (d) tracking movement of the navigation sensor based on signals generated in response to movement of the navigation sensor within the electromagnetic field.

EXAMPLE 25

The method of Example 24, further comprising (a) advancing the dilator along the guidewire to position the dilator in an anatomical passageway within the head of the patient; and (b) expanding the dilator to thereby dilate the anatomical passageway.

EXAMPLE 26

The method of Example 25, wherein the anatomical passageway is selected from the group consisting of a sinus ostium, a frontal recess, or a Eustachian tube.

EXAMPLE 27

A method of using the apparatus of Example 20, the method comprising inserting a distal portion of the apparatus into a head of a patient, wherein the distal portion includes the distal coil.

EXAMPLE 28

The method of Example 27, further comprising: (a) advancing a dilator along the distal portion of the apparatus to position the dilator in an anatomical passageway within the head of the patient; and (b) expanding the dilator to thereby dilate the anatomical passageway.

EXAMPLE 29

The method of Example 29, wherein the anatomical passageway is selected from the group consisting of a sinus ostium, a frontal recess, or a Eustachian tube.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized, In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required, Accordingly, the scope of the present invention should be considered in terms of the following claims and is understood not to be limited to the details of structure and operation shown and described in the specification and drawings.

We claim:

1. An apparatus comprising:
   (a) a proximal coil distally extending and terminating into an interlocking portion thereof such that the interlocking portion of the proximal coil defines a proximal inner diameter, wherein the proximal coil is formed by a wire wrapped in a helical configuration, wherein the proximal coil comprises:
   (i) a proximal portion,
   (ii) a distal portion extending along a longitudinal axis wherein the distal portion terminates into the interlocking portion, and
   (iii) a preformed bend located between the proximal portion and the distal portion, wherein the interlocking portion is distal relative to the preformed bend:
   (b) a distal coil defining a distal inner diameter, wherein the distal coil extends along the longitudinal axis of the distal portion, wherein the distal inner diameter along an entirety of the distal coil is larger than the proximal inner diameter, wherein the distal coil is formed by a wire wrapped in a helical configuration, wherein at least one wrap at a proximal portion of the distal coil is interlocked with the interlocking portion of the proximal coil and at least one wrap at the distal portion of the proximal coil such that interlocking portions of the proximal and distal coils form a double helix configuration and include the interlocking portion of the proximal coil;
   (c) a navigation sensor received within the distal inner diameter and located within the distal coil, wherein the navigation sensor is configured to generate signals in response to movement within an electromagnetic field; and
   (d) a wire extending through the proximal coil, wherein the wire is in electrical communication with the navigation sensor such that the wire is configured to communicate signals from the navigation sensor.

2. The apparatus of claim 1, further comprising a tubular member joined to a proximal end of the proximal coil, wherein the wire further extends through the tubular member.

3. The apparatus of claim 2, wherein the tubular member is formed of a metal material.

4. The apparatus of claim 2, further comprising a core wire, wherein the core wire is formed of a non-extensible material, wherein a proximal end of the core wire is secured to the tubular member.

5. The apparatus of claim 4, wherein a distal terminal end of the core wire is secured to the distal coil.

6. The apparatus of claim 1, further comprising a ground wire, wherein the ground wire is secured to the proximal coil, wherein the ground wire is configured to provide electrical ground to the proximal coil.

7. The apparatus of claim 1, further comprising a core wire extending to a terminal distal end of the core wire, wherein the core wire is formed of a non-extensible material, wherein the core wire extends through the preformed bend of the proximal coil and the terminal distal end of the core wire is secured to the outer coil.

8. The apparatus of claim 7, wherein the core wire has a first region with a first outer diameter, a second region with a second outer diameter, and a taper proximally positioned from the terminal distal end and extending from the first region to the second region.

9. The apparatus of claim 8, wherein the first outer diameter is proximal to the preformed bend.

10. The apparatus of claim 9, wherein the taper is proximal to the preformed bend.

11. The apparatus of claim 1, wherein the interlocking portion of the proximal coil defines a proximal outer diameter, wherein the distal coil defines a distal outer diameter, wherein the proximal outer diameter of the proximal coil is equal to the distal outer diameter of the distal coil.

12. The apparatus of claim 11, wherein the proximal outer diameter of the proximal coil is 0.0345 inches, wherein the distal outer diameter of the distal coil is 0.0345 inches.

13. The apparatus of claim 1, wherein the proximal inner diameter of the proximal coil is 0.0225 inches, wherein the distal inner diameter of the distal coil is 0.0265 inches.

14. The apparatus of claim 1, wherein the navigation sensor comprises a single axis coil.

15. The apparatus of claim 1, further comprising:
   (a) a guide member, wherein the proximal and distal coils are configured to translate relative to the guide member; and
   (b) a dilation catheter slidably disposed about the proximal coil, wherein the dilation catheter includes an expandable dilator.

16. The apparatus of claim 11, wherein the distal outer diameter along an entirety of the distal coil is constant and equal to the proximal outer diameter.

17. An apparatus, comprising:
   (a) a body;
   (b) a guide extending distally from the body;
   (c) a guidewire slidably disposed relative to the guide, wherein the guidewire comprises:
      (i) a proximal coil distally extending and terminating into an interlocking portion thereof, wherein the proximal coil is formed by a wire wrapped in a helical configuration, wherein the proximal coil comprises:
         (A) a proximal portion extending along a first axis,
         (B) a distal portion extending along a second axis wherein the distal portion terminates into the interlocking portion, and
         (C) a preformed bend located between the proximal portion and the distal portion such that the first axis and the second axis define an angle, wherein the interlocking portion is distal relative to the preformed bend:
      (ii) a distal coil extending along the second axis, wherein the distal coil is formed by a wire wrapped in a helical configuration, wherein at least one wrap at a proximal portion of the distal coil is interlocked with the interlocking portion of the proximal coil and at least one wrap at the distal portion of the proximal coil, such that interlocking portions of the proximal and distal coils form a double helix configuration and include the interlocking portion of the proximal coil,
      (iii) a joint securement positioned at the interlocking portions of the proximal and distal coils securing the interlocking portions of the proximal and distal coils together, and
      (iv) a navigation sensor located within the distal coil adjacent to the joint securement and the interlocking portions of the proximal and distal coils, wherein the navigation sensor is configured to generate signals in response to movement within an electromagnetic field; and
   (d) a dilation catheter slidably disposed relative to the guidewire, wherein the dilation catheter includes an expandable dilator.

18. The apparatus of claim 17, further comprising an image guidance system in communication with the navigation sensor, wherein the image guidance system is configured to render an image with a representation of a position of the navigation sensor in relation to a patient.

19. An apparatus comprising:
   (a) a proximal coil distally extending and terminating into an interlocking portion thereof, wherein the proximal coil is formed by a wire wrapped in a helical configuration, wherein the proximal coil comprises:
      (i) a proximal region extending along a first axis,
      (ii) a distal region extending along a second axis, wherein the distal region terminates in the interlocking portion, and
      (iii) a bent region located between the proximal region and the distal region such that the first axis and the second axis intersect to define an angle:
   (b) a distal coil, wherein the distal coil is formed by a wire wrapped in a helical configuration, wherein at least one wrap at a proximal portion of the distal coil is interlocked with the interlocking portion of the proximal coil at least one wrap at the distal region of the proximal coil, such that interlocking portions of the proximal and distal coils form a double helix configuration that extends along the second axis and include the interlocking portion of the proximal coil;
   (c) a core wire extending through the proximal coil to a terminal distal wire end thereof, wherein the terminal distal wire end is positioned at the interlocking portions of the proximal and distal coils, wherein the core wire has a first region with a first outer diameter, a second region with a second outer diameter, and a taper extending from the first region to the second region, wherein the first outer diameter is proximal to a preformed bend; and
   (d) a joint securement positioned at the terminal distal wire end and the interlocking portions of the proximal and distal coils collectively securing the interlocking portions of the proximal and distal coils and the terminal distal wire end together.

* * * * *